United States Patent

Naumann et al.

[11] Patent Number: 5,696,296
[45] Date of Patent: Dec. 9, 1997

[54] DIPHOSPHINES AND PROCESS FOR THEIR PREPARATION

[75] Inventors: Christoph Naumann, Niedernhausen; Dieter Regnat, Eppstein, both of Germany

[73] Assignee: Hoechst Aktiengesellschaft, Frankfurt, Germany

[21] Appl. No.: 534,391

[22] Filed: Sep. 27, 1995

[30] Foreign Application Priority Data

Sep. 29, 1994 [DE] Germany ............... 44 34 844.4

[51] Int. Cl.⁶ .................................... C07F 9/50
[52] U.S. Cl. ............................. 568/17; 568/16
[58] Field of Search .......................... 568/16, 17

[56] References Cited

U.S. PATENT DOCUMENTS

| | | | |
|---|---|---|---|
| 4,755,624 | 7/1988 | Phillips et al. | 568/454 |
| 4,879,416 | 11/1989 | Puckette et al. | 568/13 |
| 5,481,045 | 1/1996 | Bahrmann et al. | 568/454 |

FOREIGN PATENT DOCUMENTS

| | | |
|---|---|---|
| 0 571 819 | 12/1993 | European Pat. Off. |
| 0 653 432 | 5/1995 | European Pat. Off. |
| 87/07600 | 12/1987 | WIPO |

OTHER PUBLICATIONS

CAS 117:150499 (1992).

Primary Examiner—C. Warren Ivy
Assistant Examiner—Jean F. Vollano
Attorney, Agent, or Firm—Connolly and Hutz

[57] ABSTRACT

A diphosphine of the formula (I)

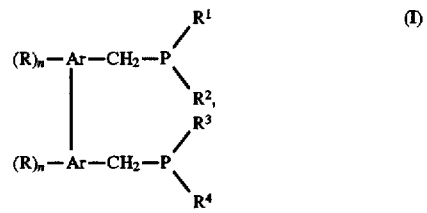

in which Ar—Ar is a biphenyl radical, a 1-phenyl-naphthyl radical or a 1,1'-binaphthyl radical, the $CH_2$ groups am each located in the ortho-position relative to the Ar—Ar bond, R is F or an alkyl radical or alkoxy radical having in each case 1 to 8 carbon atoms, n is an integer from 0 to 4, the radicals $PR^1R^2$ and $PR^3R^4$ differ from one another, $R^1$, $R^2$, $R^3$ and $R^4$ independently of one another are each an alkyl radical having 1 to 10 carbon atoms, a cycloaliphatic radical having 5 to 10 carbon atoms, or a radical $Ar^1$—$(R^5)_m$, in which $AR^1$ is a phenyl radical, $R^5$ is F, $CF_3$, or an alkyl radical having 1 to 4 carbon atoms and m is 0 to 1, or $R^1$, $R^2$, $R^3$ and $R^4$ independently of one another and including the particular P atom to which they are bonded, form a ring having 4 to 8 members, onto which one or two aromatic rings or ring systems containing 6 to 10 carbon atoms are optionally fused. The invention furthermore relates to a process for the preparation of these diphosphines.

26 Claims, No Drawings

DIPHOSPHINES AND PROCESS FOR THEIR PREPARATION

The present invention relates to compounds from the series consisting of diphosphines, a process for their preparation and their use.

Phosphanes generally have found broad industrial uses. For example, they are suitable as antioxidants, metal extraction agents, flameproofing impregnating agents, stabilizing agents for olefins (US-6-400,168 NTIS; Chem. Abstr. 100; 122286b) and trioxane (U.S. Pat. No. 4,125,540), starting compounds for Wittig reagents or ligands for metal complex catalysts.

Because of the diversity of their forms, they are also, precursors for the preparation of other optionally phosphorus-containing organic compounds.

Within the group of phosphanes, the diphosphines play a prominent role because of their material properties. Since their molecule contains two trivalent phosphorus atoms, they have complexing properties with respect to numerous metals and metal ions, especially those of the transition metal series. This ability to form complexes is a consequence of the formation of comparatively stable chelates and can be utilized for the preparation of corresponding metal complex catalysts which are used in industrial processes.

EP 0 326 286 relates to a process for the preparation of bidentate ligands of the formula (A)

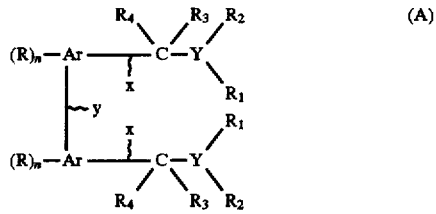

in which Ar is an aromatic ring compound, for example phenyl, naphthyl, phenanthryl and anthracenyl, the bonds designated x and y are on adjacent carbon atoms of the ring compound, R, $R_1$ and $R_2$ are a number of customary organic substituents, n is an integer from 0 to 4, 0 to 6 or 0 to 8, $R_3$ and $R_4$ are H or $R_1$, and Y is one of the elements P, As, Sb or Bi.

A compound of the formula (B)

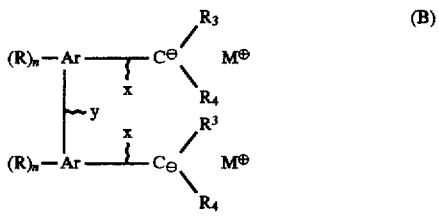

in which $M^+$ is $Li^+$, $Na^+$, $K^+$ or $Cs^+$, is reacted with a compound of the formula (C)

in which X' is halogen, to give symmetrically substituted bidentate compounds, or symmetrically substituted diphosphines if Y is phosphorus. Such symmetrically substituted bidentate compounds in association with rhodium are active catalysts for the hydroformylation of olefins carried out, in particular, under a low pressure.

In addition to symmetrically substituted diphosphines, unsymmetrically substituted diphosphines are also becoming increasingly of interest. Thus, in addition to symmetrically substituted bisphosphinoalkanes, unsymmetrically substituted bisphosphinoalkanes in particular are also gaining importance in industrial processes, for example in the selective preparation of ethanol from methanol, carbon monoxide and hydrogen (U.S. Pat. No. 4,227,200).

In view of the particular importance attributed to compounds from the series consisting of diphosphines, it is a worthwhile object to provide novel compounds from this group of substances so that the spectrum of their possible uses not only can be supplemented but also can be enriched and extended by modification of material properties and variation of structural features. In particular, it is an interesting challenge to combine the particular properties of symmetrically substituted diphosphines with the advantageous effects which result from unsymmetric substitution and therefore from steric and/or electronic effects or an additionally resulting chirality such that novel compounds are obtained which embrace an even greater or different range of uses than the symmetrically substituted diphosphines. This object is achieved by diphosphines of the formula (I)

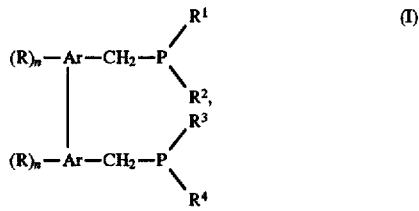

in which Ar—Ar is a biphenyl radical, a 1-phenylnaphthyl radical or a 1,1'-binaphthyl radical, the $CH_2$ groups are each located in the ortho-position relative to the Ar—Ar bond, R is F or an alkyl radical or alkoxy radical having in each case 1 to 8 carbon atoms, n is an integer from 0 to 4, the radicals $PR^1R^2$ and $PR^3R^4$ differ from one another, $R^1$, $R^2$, $R^3$ and $R^4$ independently of one another are each an alkyl radical having 1 to 10 carbon atoms, a cycloaliphatic radical having 5 to 10 carbon atoms, or a radical $Ar^1$—$(R^5)_m$, in which $Ar^1$ is a phenyl or naphthyl radical, $R^5$ is F, Cl, $CF_3$, $SO_3H$, $SO_3M$ (M=Li, Na or K), a dialkylamino radical having 2 to 8 carbon atoms or an alkyl radical or alkoxy radical having in each case 1 to 8 carbon atoms and m is an integer from 0 to 5, or $R^1$, $R^2$, $R^3$ and $R^4$, independently of one another and including the particular P atom to which they are bonded, form a ring having 4 to 8 members, onto which one or two aromatic rings or ring systems comprising 6 to 10 carbon atoms are optionally fused.

The diphosphines of the formula (I) are interesting compounds because of their chemical properties, which are probably to be attributed to the incorporation of two trivalent P atoms into the molecule, and because of their particular structure. The particular structure of the phosphanes is a result on the one hand of the —$H_2C$—$Ar(R)_n$—$Ar(R)_n$—$CH_2$-radical and on the other hand of the two different radicals $PR^1R^2$ and $PR^3R^4$. The two differing radicals $PR^1R^2$ and $PR^3R^4$ mean that the diphosphines of the formula (I) are unsymmetrically substituted compounds.

A particular feature of the novel diphosphines, furthermore, is that many of these diphosphines have one or more centers of asymmetry. In a number of cases, one of the tertiary P atoms or both tertiary P atoms can function as a center of asymmetry. In a large number of compounds, however, centers of asymmetry which result from the —$H_2C$—$Ar(R)_n$—$Ar(R)_n$—$CH_2$-grouping are also present.

The novel unsymmetrically substituted diphosphines of the formula (I) therefore also open up access to the corresponding optically active isomers, for example to diastereomeric diphosphines or to enantiomeric diphosphines, which in turn can be used, inter alia, as auxiliaries in carrying out asymmetric syntheses.

Because of their chemical behaviour and their reactivity and because of their particular structure, the novel diphosphines are in addition suitable units for the preparation of other optionally phosphorus-containing organic compounds.

Diphosphines of the formula (I) in which Ar—Ar is a biphenyl radical, a 1-phenylnaphthyl radical or a 1,1'-binaphthyl radical and R is an alkyl radical or alkoxy radical having in each case I to 4 carbon atoms play a particular role since they are comparatively readily accessible.

This also applies to diphosphines of the formula (I) in which n is 0 or 1, in particular 0.

Diphospanes in which $R^1$ and $R^2$ are identical or different and independently of one another are an alkyl radical having 1 to 6 carbon atoms, a cycloaliphatic radical having 5 to 6 carbon atoms or a radical $Ar^1$—$(R^5)_m$, in which $Ar^1$ is a phenyl radical, $R^5$ is F, $CF_3$ or an alkyl radical having 1 to 4 carbon atoms and m is 0 or 1, or $R^1$ and $R^2$, together with the P atom, form a ring and are $CH_2$—$Ar(R)_n$—$Ar(R)_n$—$CH_2$ are also of interest. The radicals $R^3$ and $R^4$ are chosen from the same group of radicals as $R^1$ and $R^2$, but with the condition that the radical $PR^1R^2$ differs from the radical $PR^3R^4$.

Diphosphines in which $R^3$ and $R^4$ are identical or different and independently of one another are an alkyl radical having 1 to 6 carbon atoms, a cycloaliphatic radical having 5 to 6 carbon atoms or a radical $Ar^1$—$(R^5)_m$, in which $Ar^1$ is a phenyl radical, $R^5$ is F, $CF_3$ or an alkyl radical having 1 to 4 carbon atoms and m is 0 or 1, or $R^3$ and $R^4$, together with the P atom, form a ring and are $CH_2$—$Ar(R)_n$—$Ar(R)_n$—$CH_2$ are furthermore of interest.

If the diphosphines of the formula (I) have a center of asymmetry and thus meet the conditions for the existence of optical isomers, they are in the (R,S) form, in the (R) form or in the (S) form. Diphosphines in the (R) form and the (S) form are of interest in connection with carrying out asymmetric syntheses.

They can be used either in the (R) form or (S) form as optically active units, with a good prospect of success, for synthesizing other optionally optically active and optionally phosphorus-containing compounds in the (R) form or (S) form.

Diphosphines of the formula (I) in which Ar—Ar is 1,1'-binaphthyl and the diphosphane is in the (R,S) form, the (R) form or the (S) form and n is optionally 0 or 1, in particular 0, are of particular interest. These compounds not only are readily accessible in the (R,S) form, but can also be prepared with justifiable expenditure in the (R) form as well as in the (S) form.

The following compounds may be mentioned as typical representatives of diphosphines of the formula (I), without claiming completeness:

2-Diphenylphosphinomethyl-2'-diisopropylphosphinomethyl-biphenyl

2-Diphenylphosphinomethyl-2'-dihutylphosphinomethyl-biphenyl

2-Diphenylphosphinomethyl-2'-di-sec-butylphosphinomethyl-biphenyl

2-Diphenylphosphinomethyl-2'-dicyclohexylphosphinomethyl-biphenyl

2-Diphenylphosphinomethyl-2'-[his(2-tolyl)phosphinomethyl]biphenyl

2-Diphenylphosphinomethyl-2'-[bis(4-fluorophenyl)phosphinomethyl]biphenyl

2-Diphenylphosphinomethyl-2'-diisopropylphosphinomethyl-1,1'-binaphthyl

2-Diphenylphosphinomethyl-2'-di-sec-butylphosphinomethyl-1,1'-binaphthyl

2-Diphenylphosphinomethyl-2'-di-n-butylphosphinomethyl-1,1'-binaphthyl

2-Diphenylphosphinomethyl-2'-dicyclohexylphosphinomethyl-1,1'-binaphthyl

2-Diphenylphosphinomethyl-2'-[bis(2-tolyl)phosphinomethyl]-1,1'-binaphthyl

2-Diphenylphosphinomethyl-2'-[bis(4-fluorophenyl)-phosphinomethyl]-1,1'-binaphthyl 2-Diphenylphosphinomethyl-2'-methylphenylphosphinomethyl-1,1'-binaphthyl 2-Diphenylphosphinomethyl-2'-cyclohexylphenylphosphino-methyl-1,1'-binaphthyl 2-Diisopropylphosphinomethyl-2'-di-sec-butylphosphinomethyl-1,1'-binaphthyl 2-Diisopropylphosphinomethyl-2'-di-n-butylphosphinomethyl-1,1'-binaphthyl 2-Diisopropylphosphinomethyl-2'-dicyclohexylphosphinomethyl-1,1'-binaphthyl 2-Diisopropylphosphinomethyl-2'-[bis(2-tolyl)phosphinomethyl]-1,1'-binaphthyl 2-Diisopropylphosphinomethyl-2'-[bis(4-fluorophenyl)phosphinomethyl]-1,1'-binaphthyl 2-Diisopropylphosphinomethyl-2'-methylphenylphosphinomethyl-1,1'-binaphthyl 2-Diisopropylphosphinomethyl-2'-cyclohexylphenylphosphinomethyl-1,1'-binaphthyl 2-Dicyclohexylphosphinomethyl-2'-di-sec-butylphosphinomethyl-1,1'-binaphthyl 2-Dicyclohexylphosphinomethyl-2'-di-n-butylphosphinomethyl-1,1'-binaphthyl 2-Dicyclohexylphosphinomethyl-2'-[bis(2-tolyl)phosphinomethyl]-1,1'-binaphthyl 2-Dicyclohexylphosphinomethyl-2'-[bis(4-fluorophenyl)-phosphinomethyl]-1,1'-binaphthyl 2-Dicyclohexylphosphinomethyl-2'-methylphenylphosphino-methyl-1,1'-binaphthyl 2-Dicyclohexylphosphinomethyl-2'-cyclohexylphenylphosphinomethyl-1,1'-binaphthyl 2-Cyclohexylphenylphosphinomethyl-2'-methylphenylphosphinomethyl-1,1'-binaphthyl The present invention relates to a process for the preparation of diphosphines of the formula (I)

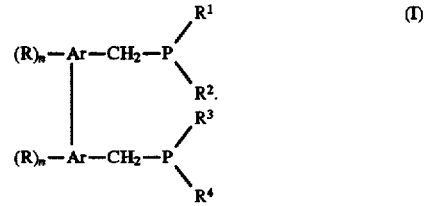

It comprises reacting a compound of the formula (II)

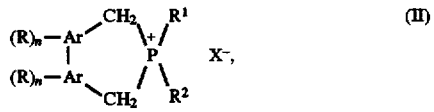

in which Ar—Ar is a biphenyl radical, a 1-phenylnaphthyl radical or a 1,1'-binaphthyl radical, the $CH_2$ groups are each located in the ortho-position relative to the Ar—Ar bond, R is F or an alkyl radical or alkoxy radical having in each case 1 to 8 carbon atoms, n is an integer from 0 to 4, $R^1$ and $R^2$ are identical or different and independently of one another are an alkyl radical having 1 to 10 carbon atoms, a cycloaliphatic radical having 5 to 10 carbon atoms, or a radical $Ar^1$—$(R^5)_m$, in which $Ar^1$ is a phenyl or naphthyl radical, $R^5$ is F, Cl, $CF_3$, $SO_3H$, $SO_3M$ (M=Li, Na or K), a dialkylamino radical having 2 to 8 carbon atoms or an alkyl radical or alkoxy radical having in each case 1 to 8 carbon atoms and m is an integer from 0 to 5, or $R^1$ and $R^2$, together with the P atom, form a ring having 4 to 8 members, onto which one or two aromatic rings or ring systems comprising 6 to 10 carbon atoms are optionally fused, and $X^-$ is a monovalent anion or the equivalent of a polyvalent anion of a mineral acid, carboxylic acid, sulfonic acid or alcohol, with a compound of the formula (III)

in which Me is a metal, $R^3$ and $R^4$ are identical or different and are chosen independently of one another from the same group of radicals as $R^1$ and $R^2$ and p is 1 or 2, in the presence of a solvent at $-20°$ to $160°$ C.

The reaction proceeds according to the following equation:

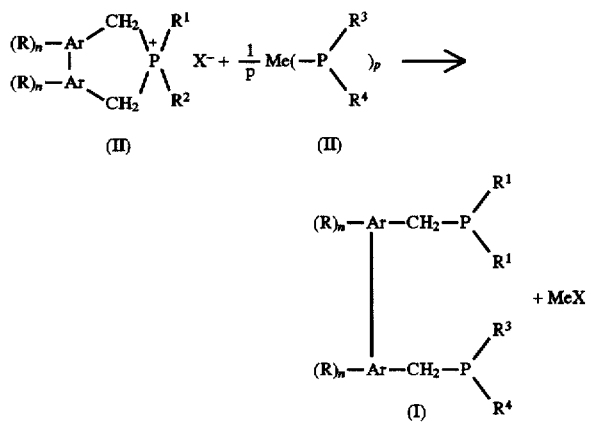

in which R, n, Ar—Ar, $R^1$, $R^2$, $R^3$, $R^4$, X, Me and p have the abovementioned meaning.

One advantage of the process according to the invention is that comparatively readily accessible starting substances can be used. This applies both to the compounds of the formula (II) and to the compounds of the formula (III). Another advantage is that the reaction can be realized without great expenditure on apparatus. Furthermore, the reaction proceeds with a high selectivity and gives the desired end products (compounds of the formula (I)) in a high yield. The purity of the end products thereby obtained is usually so good that a very pure end product can already be obtained by simple crystallization from the reaction mixture obtained directly. An additional purification, which requires further technical expenditure and as a rule results in a reduction in yield, can be dispensed with in this case.

The process is not only limited to the preparation of unsymmetrically substituted diphosphines. It can also be used with good success for the preparation of symmetrically substituted diphosphines, for example using Me—$(PR^1R^2)_p$ as the compound of the formula (III). An essential advantage of the process is that unsymmetrically substituted diphosphines of the formula (I) can be prepared in a targeted manner without having to accept the formation of mixtures of symmetrically substituted diphosphines and unsymmetrically substituted diphosphines which are difficult to separate. Such mixtures are always formed if each individual radical $PR^1R^2$ and $PR^3R^4$ is not successfully inserted into the molecule with a high selectivity. In this connection, it should be pointed out that EP 0 326 286 mentioned at the outset only describes a process for the preparation of symmetrically substituted diphosphines with two identical radicals $YR^1R^2$ (Y=P, As, Sb or Bi). A process for the preparation of unsymmetrically substituted diphosphines of the formula (I) is not to be found in EP 0 326 286.

Compounds of the formula (II) in which Ar—Ar is a biphenyl radical, a 1-phenylnaphthyl radical or a 1,1-binaphthyl radical and R is an alkyl radical or alkoxy radical having in each case 1 to 4 carbon atoms play a particular role for the process since they are comparatively readily accessible and a quite wide selection of them can be made available. This also applies to compounds of the formula (II) in which n is 0 or 1, in particular 0.

Another advantage of the process according to the invention is to be seen in the fact that in a number of cases optically active diphosphines of the formula (I) can be prepared both in the (R) form and in the (S) form.

It is generally known that it is very difficult to separate a racemic mixture into enantiomerically pure or even only largely enantiomerically pure compounds. Such resolutions of racemates are in general associated with a very high degree of complexity, and furthermore usually are not successful.

By reaction of the compound of the formula (II) in the (R) form or in the (S) form in accordance with the equation described above, the process according to the invention surprisingly opens up a very simple route for the direct preparation of diphosphines of the formula (I) in the (R) form and the (S) form. Since the (R) and the (S) form of the phosphonium salts used as starting substances can be synthesized in a targeted manner and the reaction, with ring-opening, of the phosphonium salts (II) does not lead to racemization or to complete splitting off of a phosphorus-containing organic compound, expensive resolution of racemates, the prospects of success of which furthermore are very uncertain, can be dispensed with. The enantiomerically pure or largely enantiomerically pure phosphonium salts can be obtained directly from the reaction mixture by simple crystallization and can be isolated by filtration.

A compound of the formula (II) is employed in the (R,S) form, in the (R) form or in the (S) form, as required, to give the corresponding diphosphane in the (R,S) form, in the (R) form or in the (S) form.

It is of particular interest to employ compounds of the formula (II) in which Ar—Ar is 1,1-binaphthyl in the (R,S) form, in the (R) form and in the (S) form. It is especially interesting to employ these compounds in the (R) form or the (S) form, in order to prepare the corresponding diphosphines.

In a large number of cases, a compound of the formula (II) in which $R^1$ and $R^2$ are identical or different and independently of one another are an alkyl radical having 1 to 6 carbon atoms, a cycloaliphatic radical having 5 to 6 carbon atoms or a radical $Ar^1$—$(R^5)_m$, in which $Ar^1$ is a phenyl radical, $R^5$ is F, $CF_3$ or an alkyl radical having 1 to 4 carbon atoms and m is 0 or 1, or $R^1$ and $R^2$, together with the P atom, form a ring and are $CH_2$—$Ar(R)_n$—$Ar(R)_n$—$CH_2$ is employed.

The compound of the formula (II) is reacted with a compound of the formula (III) in which Me, as already mentioned above, is a metal, in particular an alkali metal or alkaline earth metal, for example Li, Na, K, Mg or Ca, preferably Na or K.

In a large number of cases, a compound of the formula (III) in which $R^3$ and $R^4$ are identical or different and independently of one another are an alkyl radical having 1 to 6 carbon atoms, a cycloaliphatic radical having 5 to 6 carbon atoms or a radical $Ar^1$—$(R^5)_m$, in which $Ar^1$ is a phenyl radical, $R^5$ is F, $CF_3$ or an alkyl radical having 1 to 4 carbon atoms and m is 0 or 1, or $R^3$ and $R^4$, together with the P atom, form a ring and are $CH_2$—$Ar(R)_n$—$Ar(R)_n$—$CH_2$ is employed.

A compound of the formula (III) in which $R^3$ and $R^4$ are identical or different and independently of one another are an alkyl radical having 1 to 6 carbon atoms, a cycloaliphatic radical having 5 to 6 carbon atoms or a radical $Ar^1$—$(R^5)_m$, in which $Ar^1$ is a phenyl radical, $R^5$ is F, $CF_3$ or an alkyl radical having 1 to 4 carbon atoms and m is 0 or 1 is employed in particular.

The reaction is carried out in the presence of a solvent, in particular an organic solvent which is inert under the conditions of the reaction. A polar aprotic solvent or a mixture of polar aprotic solvents is usually used as the solvent. Suitable polar aprotic solvents are, without claiming completeness, N,N-dimethylformamide, tetrahydrofuran, dioxane or mixtures thereof. N,N-dimethylformamide has proved to be a particularly suitable solvent in a number of cases.

It is possible to suspend or dissolve both the compound of the formula (II) and the compound of the formula (III) in the solvent or solvent mixture and then to react them. Usually, the solvent or solvent mixture is added to the compound of the formula (II), this solution or suspension is initially introduced into the reaction vessel and the compound of the formula (III) is added in dissolved form. Good thorough mixing, for example by stirring, is to be ensured for carrying out the reaction. As a rule, it is sufficient to react the compound of the formula (II), that is to say the phosphonium salt, and the compound of the formula (III), that is to say the phosphide, in a molar ratio of (1 to 2):1, in particular (1 to 1.2):1. As mentioned above, the reaction is carried out at −20° to 160° C. Temperatures of 0 to 120, in particular 10° to 100° C., have often proved to be sufficient for carrying out the reaction. When the reaction has ended, the solvent is removed by distillation under reduced pressure and a non-polar solvent is added to the reaction product obtained, if necessary and desired. Suitable non-polar solvents are toluene, o-xylene, m-xylene, p-xylene, mixtures of isomeric xylenes, ethylbenzene, mesitylene, aliphatic hydrocarbons or mixtures of these solvents.

The addition of the non-polar solvent serves to dissolve the desired valuable product and to separate it off from undissolved salts by means of filtration. The filtrate obtained is concentrated, the desired valuable product already crystallizing out in a high purity.

The process according to the invention can generally be carried out continuously or batchwise. It is particularly suitable for a batchwise procedure.

The diphosphines of the formula (I) are suitable as antioxidants and constituents of catalyst systems.

The following examples describe the invention, without limiting it.

EXPERIMENTAL PART

Example 1

Preparation of (R,S)-2,2'-bis (diphenylphosphinomethyl)-1,1'-binaphthyl 1.4 g (7.4 mmol) of diphenylphosphine are dissolved in 20 ml of N,N-dimethylformamide (DMF). 0.36 g of sodium hydride (50% strength suspension in paraffin oil) is added and the mixture is stirred at room temperature for 12 hours. This solution of the compound of the formula (III) is then slowly added dropwise to 4.0 g (7.3 mmol) of (R,S)-4,4-diphenyl-4,5-dihydro-3H-dinaphtho[2,1-c:1',2'-e] phosphepiniumbromide (compound of the formula (II)) suspended in 40 ml of DMF. The resulting red solution is stirred at room temperature for 24 hours. The DMF is then removed at 50° C./$10^{-2}$ mmHg. The residue is taken up in 120 ml of toluene, 0.3 ml of water is added and the mixture is stirred for 30 minutes. The precipitate which has separated out is filtered off (0.9 g) and the toluene is removed at 50° C./$10^{-2}$ mmHg. For purification, 10 ml of acetone are added to the residue and the resulting crystals are filtered off under an inert gas. 4 ml of i-propanol are added to the acetone mother liquor and the mixture is cooled at 0° C. for several hours. The resulting precipitate is filtered off again.

Yield: 3.4 g (71.3%)

Melting point: 156° C.

$^{31}$P-NMR spectrum: (CDCl$_3$) −12.3 ppm

Example 2

Preparation of (R,S)-2-(diphenylphosphino)-2'-(dicyclo-hexylphosphino)methyl-1,1'-binaphthyl 3 g (5.4 mmol) of (R,S)-4,4-dicyclohexyl-4,5-dihydro-3H-dinaphtho[2,1-c:1', 2'-e]phosphepinium bromide (compound of the formula (II)) are reacted analogously to Example 1.

The crude product is dissolved with 8 ml of n-heptane at the boiling point and the solution is left to stand for several hours for crystallization.

Yield: 2.5 g (70.1%)

Melting point: 121° C.

$^{31}$P-NMR spectrum: (CDCl$_3$)+1.32 ppm, −12.3 ppm

Mass spectrum: M$^+$=662

Example 3

Preparation of 2-(diphenylphosphino)-2'-(diisopropyl-phosphino)methyl-1,1'-binaphthyl 4 g (8.4 mmol) of (R,S)-4,4-diisobutyl-4,5-dihydro-3H-dinaphtho[2,1-c:1', 2'-e]phosphepinium bromide (compound of the formula (II)) are reacted analogously to Example 1. The crude product is dissolved with 25 ml of n-heptane at the boiling point and the solution is left to stand for several hours. The supernatant solution is decanted off and the resulting oil is dried at 70° C./$10^{-2}$ mmHg.

Yield: 3.6 g (75.0%); oil $^{31}$P-NMR spectrum: (CDCl$_3$) +9.0 ppm, −12.4 ppm

Mass spectrum: M$^+$=583

Example 4

Preparation of (S)-2,2'-bis (diphenylphosphinomethyl)-1,1'-binaphthyl 1 g (1.83 mmol) of (S)-4,4-diphenyl-4,5-dihydro-3H-dinaphtho[2,1-c:1', 2'-e]phosphepinium bromide (compound of the formula (II)) are reacted analogously to Example 1.

Yield: 710 mg (60%)

Melting point: 155°–156° C.

$^{31}$P-NMR spectrum: (CDCl$_3$) −12.3 ppm $[\alpha]^{20}_D$=−14.7° (measured in methylene chloride)

Example 5

Preparation of (R,S)-2,2'-bis (diphenylphosphinomethyl)-1,1'-binaphthyl 35 ml of a 0.5 molar solution of potassium diphenylphosphide in tetrahydrofuran (THF), corresponding to 17.5 mmol of potassium diphenyl phosphide (compound of the formula (III)), are initially introduced into the reaction vessel and 100 ml of absolute N,N-dimethylformamide (DMF) are added at room temperature. 9 g (16.14 mmol) of (R,S)-4,4-diphenyl-4,5-dihydro-3H-di-naphtho[2,1-c:1', 2'-e] phosphepiniumbromide (compound of the formula (II)) in solid form are then added. The red solution which thereby forms is stirred at room temperature for 12 hours. Thereafter, the solvent mixture comprising THF and DMF is removed at 50° C./10$^{-2}$ mmHg. The residue is taken up in 100 ml of methylene chloride and the solid is filtered off. The methylene chloride is removed at 30° C./10$^{-2}$ mmHg. The residue is heated in 20 ml of iso-propanol and left to stand for crystallization. The supernatant solution is decanted off. The residue is taken up in 35 ml of n-heptane and the solid still present is filtered off at the boiling point. The filtrate is allowed to cool slowly for crystallization of the product.

Yield: 8.0 g (75%)

Melting point: 125° C.

$^{31}$P-NMR spectrum: (CDCl$_3$) +1.34 ppm, −12.3 ppm

We claim:

1. A diphosphine of the formula (I)

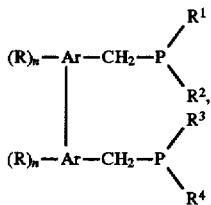

in which Ar—Ar is a biphenyl radical, a 1-phenyl-naphthyl radical or a 1,1'-binaphthyl radical, the CH$_2$ groups are each located in the ortho-position relative to the Ar—Ar bond, R is F or an alkyl radical or alkoxy radical having in each case 1 to 8 carbon atoms, n is an integer from 0 to 4, the radicals PR$^1$R$^2$ and PR$^3$R$^4$ differ from one another, R$^1$, R$^2$, R$^3$ and R$^4$ independently of one another are each an alkyl radical having 1 to 10 carbon atoms, a cycloaliphatic radical having 5 to 10 carbon atoms, or a radical Ar$^1$—(R$^5$)$_m$, in which Ar$^1$ is a phenyl radical, R$^5$ is F, CF$_3$, or an alkyl radical having 1 to 4 carbon atoms and m is 0 to 1, or R$^1$, R$^2$, R$^3$ and R$^4$ independently of one another and including the particular P atom to which they are bonded, form a ring having 4 to 8 members, onto which one or two aromatic rings or ring systems comprising 6 to 10 carbon atoms are optionally fused.

2. A diphosphine as claimed in claim 1, in which Ar—Ar is a biphenyl radical, a 1-phenylnaphthyl radical or a 1,1'-binaphthyl radical and R is an alkyl radical or alkoxy radical having in each case 1 to 4 carbon atoms.

3. A diphosphine as claimed in claim 1, in which n is 0 or 1.

4. A diphosphine as claimed in claim 1, in which n is 0.

5. A diphosphine as claimed in claim 1, in which R$^1$ and R$^2$ are identical or different and independently of one another are an alkyl radical having 1 to 6 carbon atoms, a cycloaliphatic radical having 5 to 6 carbon atoms or R$^1$ and R$^2$, together with the P atom, form a ring and are CH$_2$—Ar (R)$_n$—Ar(R)$_n$—CH$_2$.

6. A diphosphine as claimed in claim 1, in which R$^3$ and R$^4$ are identical or different and independently of one another are an alkyl radical having 1 to 6 carbon atoms, a cycloaliphatic radical having 5 to 6 carbon atoms or R$^3$ and R$^4$, together with the P atom, form a ring and are CH$_2$—Ar (R)$_n$—Ar(R)$_n$—CH$_2$.

7. A diphosphine as claimed in claim 1, which is in the (R,S) form, in the (R) form or in the (S) form.

8. A diphosphine as claimed in claim 1, in which Ar—Ar is 1,1'-binaphthyl and which is in the (R,S) form, in the (R) form or in the (S) form.

9. A process for the preparation of a diphosphine of the formula (I)

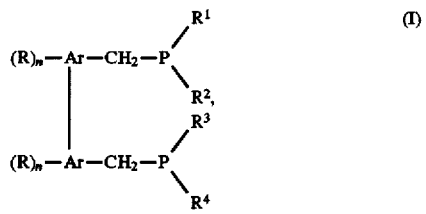

which comprises reacting a compound of the formula (II)

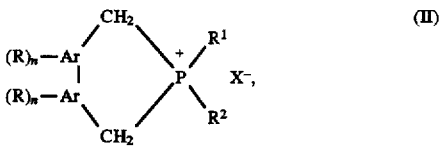

in which Ar—Ar is a biphenyl radical, a 1-phenyl-naphthyl radical or a 1,1'-binapthyl radical, the CH$_2$ Groups are each located in the ortho-position relative to the Ar—Ar bond, R is F or an alkyl radical or alkoxy radical having in each case 1 to 8 carbon atoms, n is an integer from 0 to 4, R$^1$ and R$^2$ are identical or different and independently of one another are an alkyl radical having 1 to 10 carbon atoms, a cycloaliphatic radical having 5 to 10 carbon atoms, or a radical Ar$^1$—(R$^5$)$_m$, in which Ar$^1$ is a phenyl or naphthyl radical, R$^5$ is F, Cl, CF$_3$, SO$_3$H, SO$_3$M (M=Li, Na or K), a dialkylamino radical having 2 to 8 carbon atoms or an alkyl radical or alkoxy radical having in each case 1 to 8 carbon atoms and m is an integer from 0 to 5, or R$^1$ and R$^2$, together with the P atom, form a ring having 4 to 8 members, onto which one or two aromatic rings or ring systems comprising 6 to 10 carbon atoms are optionally fused, and X$^-$ is a monovalent anion or the equivalent of a polyvalent anion of a mineral acid, carboxylic acid or sulfonic acid, with a compound of the formula (III)

in which Me is a metal, R$^3$ and R$^4$ are identical or different and are chosen independently of one another from the same group of radicals as R$^1$ and R$^2$ and p is 1 or 2, in the presence of a solvent at −20° to 160° C.

10. The process as claimed in claim 9, wherein a compound of the formula (II) in which Ar—Ar is a biphenyl radical, a 1-phenylnaphthyl radical or a 1,1'-binaphthyl radical and R is an alkyl radical or alkoxy radical having in each case 1 to 4 carbon atoms is employed.

11. The process as claimed in claim 9, wherein a compound of the formula (II) in which n is 0 or 1 is employed.

12. The process as claimed in claim 9, wherein a compound of the formula (II) in which n is 0 is employed.

13. The process as claimed in claim 9, wherein a compound of the formula (II) in the (R,S) form, in the (R) form or in the (S) form is employed.

14. A process as claimed in claim 9, wherein a compound of the formula (II) in which Ar—Ar is 1,1'-binaphthyl in the (R,S) form, in the (R) form or in the (S) form is employed.

15. The process as claimed in claim 9, wherein a compound of the formula (II) in which $R^1$ and $R^2$ are identical or different and independently of one another are an alkyl radical having 1 to 6 carbon atoms, a cycloaliphatic radical having 5 to 6 carbon atoms or a radical $Ar^1$—$(R^5)_m$, in which $Ar^1$ is a phenyl radical, $R^5$ is F, $CF_3$ or an alkyl radical having 1 to 4 carbon atoms and m is 0 or 1, or $R^1$ and $R^2$, together with the P atom, form a ring and are $CH_2$—$Ar(R)_n$—$Ar(R)_n$—$CH_2$ is employed.

16. The process as claimed in claim 9, wherein a compound of the formula (III) in which Me is Li, Na, K, Mg or Ca is employed.

17. The process as claimed in claim 9, wherein a compound of the formula (III) in which $R^3$ and $R^4$ are identical or different and independently of one another are an alkyl radical having 1 to 6 carbon atoms, a cycloaliphatic radical having 5 to 6 carbon atoms or a radical $Ar^1$—$(R^5)_m$, in which $Ar^1$ is a phenyl radical, $R^5$ is F, $CF_3$ or an alkyl radical having 1 to 4 carbon atoms and m is 0 or 1, or $R^3$ and $R^4$, together with the P atom, form a ring and are $CH_2$—$Ar(R)_n$—$Ar(R)_n$—$CH_2$ is employed.

18. The process as claimed in claim 9, wherein a compound of the formula (III) in which $R^3$ and $R^4$ are identical or different and independently of one another are an alkyl radical having 1 to 6 carbon atoms, a cycloaliphatic radical having 5 to 6 carbon atoms or a radical $Ar^1$—$(R^5)_m$, in which $Ar^1$ is a phenyl radical, $R^5$ is F, $CF_3$ or an alkyl radical having 1 to 4 carbon atoms and m is 0 or 1 is employed.

19. The process as claimed in claim 9, wherein a polar aprotic solvent or a mixture of polar aprotic solvents is employed as the solvent.

20. The process as claimed in claim 9, wherein N,N-dimethylformamide, tetrahydrofuran, dioxane or a mixture thereof is employed as the solvent.

21. The process as claimed in claim 9, wherein N,N-dimethylformamide is employed as the solvent.

22. The process as claimed in claim 9, wherein the compound of the formula (II) and the compound of the formula (III) are employed in a molar ratio of (1 to 2):1.

23. The process as claimed in claim 9, wherein the reaction is carried out at 0° to 120° C.

24. The process as claimed in claim 16, wherein Me is Na or K.

25. The process as claimed in claim 22, wherein the compound of formula (II) and the compound of the formula (III) are employed in a molar ratio of (1 to 1.2):1.

26. The process as claimed in claim 9, wherein the reaction is carried out at 10° to 100° C.

* * * * *